United States Patent
Zhang et al.

(10) Patent No.: US 11,865,194 B2
(45) Date of Patent: Jan. 9, 2024

(54) BENZENE RING-CONTAINING GLUCOSE DERIVATIVE AND USE THEREOF

(71) Applicant: Beijing Normal University, Beijing (CN)

(72) Inventors: Junbo Zhang, Beijing (CN); Qianqian Gan, Beijing (CN); Qianna Wang, Beijing (CN); Xuran Zhang, Beijing (CN); Qing Ruan, Beijing (CN); Yuhao Jiang, Beijing (CN); Xuebin Wang, Beijing (CN); Zhigang Tang, Beijing (CN); Jie Lu, Beijing (CN); Zhanbin Zhang, Beijing (CN)

(73) Assignee: Beijing Normal University, Beijing (CN)

( * ) Notice: Subject to any disclaimer, the term of this patent is extended or adjusted under 35 U.S.C. 154(b) by 0 days.

(21) Appl. No.: 18/297,575

(22) Filed: Apr. 7, 2023

(65) Prior Publication Data
US 2023/0263914 A1    Aug. 24, 2023

Related U.S. Application Data

(63) Continuation of application No. PCT/CN2021/097601, filed on Jun. 1, 2021.

(30) Foreign Application Priority Data

Oct. 13, 2020   (CN) .......................... 202011090061.3

(51) Int. Cl.
  *A61K 51/02*   (2006.01)
(52) U.S. Cl.
  CPC .................. *A61K 51/025* (2013.01)
(58) Field of Classification Search
  None
  See application file for complete search history.

(56) References Cited

U.S. PATENT DOCUMENTS

2014/0066609 A1   3/2014   Lu

FOREIGN PATENT DOCUMENTS

| CN | 101555263 A | 10/2009 |
|---|---|---|
| CN | 105001274 A | 10/2015 |
| CN | 107245087 A | 10/2017 |
| CN | 111138504 A | * 5/2020 |
| CN | 111138504 A | 5/2020 |
| CN | 112175025 A | 1/2021 |
| KR | 20140134365 A | 11/2014 |

OTHER PUBLICATIONS

Junbo Zhang et al., "A Preliminary Study On a New ^(99m)Tc Nitrido Complex With Dithiocarbamate Ligand Containing the Morpholino Group", Journal of Beijing Normal University (Natural Science), Dec. 2005, vol. 41, No. 6, pp. 613-615.

* cited by examiner

Primary Examiner — Jennifer Chin

(57) ABSTRACT

Disclosed herein is a benzene ring-containing glucose derivative of formula (I):

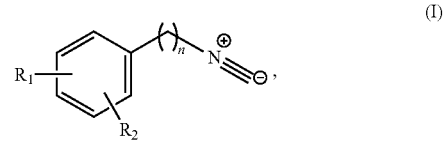

where $R_1$ is each independently

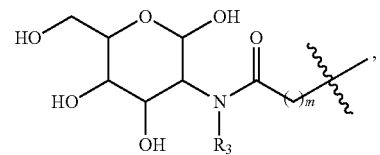

and $R_2$ is hydrogen. This application also provides a radioactive drug, including a complex formed by the benzene ring-containing glucose derivative and a radionuclide. Use of the benzene ring-containing glucose derivative in the tumor treatment and diagnosis is further provided.

5 Claims, No Drawings

BENZENE RING-CONTAINING GLUCOSE DERIVATIVE AND USE THEREOF

CROSS-REFERENCE TO RELATED APPLICATIONS

This application is a continuation of International Patent Application No. PCT/CN/2021/097601, filed on Jun. 1, 2021, which claims the benefit of priority from Chinese Patent Application No. 202011090061.3, filed on Oct. 13, 2020. The content of the aforementioned application, including any intervening amendments thereto, is incorporated herein by reference in its entirety.

TECHNICAL FIELD

This application relates to radiopharmaceutical chemistry and clinical nuclear medicine, and more particularly to a benzene ring-containing glucose derivative and a use thereof.

BACKGROUND

As a life-threatening disease, early diagnosis and treatment of cancer are of great significance for improving survival rates, reducing mortality, relieving pain, and lowering treatment costs. Nuclear medicine imaging technology is applicable to the molecular diagnosis of tumors, and due to the advantages of high sensitivity, excellent specificity, and non-invasion, it has been extensively employed in the early tumor diagnosis. Especially, in combination with computed tomography (CT), such as positron emission tomography (PET) and single photon emission computed tomography (SPECT), radionuclide tumor imaging has become dominated in the nuclear medicine diagnosis.

Glucose is the main energy source for cell metabolism. Malignant tumor cells have a higher glucose demand compared to normal cells due to rapid proliferation and high metabolic activity. Based on this, combined with nuclear medicine imaging, glucose derivatives can be labeled with radionuclides and used in tumor imaging. Currently, $^{18}$F-2-fluoro-2-deoxy-D-glucose ([$^{18}$F]FDG) is the predominant tumor imaging agent in clinic. However, the preparation of $^{18}$F requires an accelerator, which leads to high diagnosis cost, limiting its clinical application. Compared with PET, SPECT instruments are more readily available and have a lower diagnosis cost. With the application of cadmium zinc telluride (CZT) crystals in SPECT and the development of image reconstruction technology, the resolution and sensitivity of SPECT have been continuously improved. Therefore, it is urgently required to develop a new SPECT tumor imaging agent with simple preparation and low cost. $^{99m}$Tc is the most widely used SPECT nuclide in the clinical practice since it has desirable half-life ($T_{1/2}$=6.02 h), and emits 140 keV single γ-photons. Moreover, the popularization and application of $^{99}$Mo-$^{99m}$Tc generators further promote the clinical application of $^{99m}$Tc radiopharmaceuticals.

Chinese Patent Application No. 201710451094.8 (published as No. 107245087A) discloses a $^{99m}$Tc-labeled isonitrile-containing glucose derivative, and a preparation and use thereof. It has been demonstrated that the $^{99m}$Tc-labeled isonitrile-containing glucose derivative ($^{99m}$Tc-(CN5DG)$_6^+$) has a good tumor-to-nontarget ratio, but its tumor uptake still remains to be improved.

Chinese Patent Application No. 202010032704.2 (published as No. 111138504A) discloses a $^{99m}$Tc-CNPEDG complex, and a preparation and use thereof. The $^{99m}$Tc-CNPEDG complex was synthesized by introducing a benzene ring between the chelating group (isocyano group) and the targeting group (D-glucosamine). The $^{99m}$Tc-CNPEDG complex has simple preparation, higher tumor uptake and desirable retention, but fails to be quickly eliminated from the blood. Additionally, its tumor uptake and tumor-to-nontarget ratio of the $^{99m}$Tc-CNPEDG complex need to be further improved.

SUMMARY

An objective of this application is to provide a benzene ring-containing glucose derivative and a use thereof to overcome the deficiencies in the existing technologies. The glucose derivative has stable structure, simple preparation, high tumor uptake and desirable tumor-to-nontarget ratio, and can be employed in the tumor diagnosis and treatment after being radiolabeled. Therefore, this application has important scientific significance and brilliant application prospects in tumor diagnosis and treatment.

Technical solutions of this application are described as follows.

In a first aspect, this application provides a benzene ring-containing glucose derivative of formula (I):

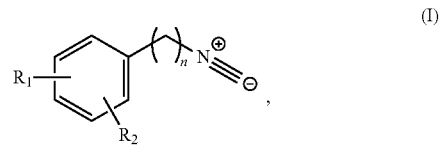

wherein one or two R$_1$ are located on a benzene ring in formula (I);

the one or two R$_1$ are each independently

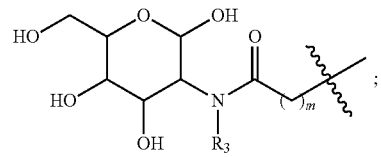

wherein R$_3$ is hydrogen, deuterium, halogen, cyan group (—CN), nitro group (—NO$_2$), C$_{1-12}$ alkyl group, C$_{2-12}$ alkenyl or C$_{2-12}$ alkynyl; m is 0 or a positive integer; and  represents chemical bonding between R$_1$ and the benzene ring in formula (I);

R$_2$ is hydrogen, deuterium, halogen, —CN, —NO$_2$, C$_{1-12}$ alkyl group, C$_{2-12}$ alkenyl or C$_{2-12}$ alkynyl;

n is 0 or a positive integer; and when m=0, n=1 and R$_3$ is hydrogen, there is one R$_1$, and R$_1$ is not on the 4-position of the benzene ring.

In an embodiment, when there is one R$_1$, R$_1$ is on 3-position or 4-position of the benzene ring in formula (I); when there are two R$_1$, the two R$_1$ are on 3-position and 4-position of the benzene ring, respectively; in R$_1$, R$_3$ is hydrogen, deuterium, halogen, C$_{1-7}$ alkyl group, C$_{2-7}$ alkenyl or C$_{2-7}$ alkynyl; and m is 0 or 1;

R$_2$ is hydrogen, deuterium, halogen, C$_{1-7}$ alkyl group, C$_{2-7}$ alkenyl or C$_{2-7}$ alkynyl;

n is 0, 1, or 2.

In an embodiment, the sum of m and n is 2 or 3.

In an embodiment, there is one R$_1$, and the one R$_1$ is on the 3-position of the benzene ring. It has been demonstrated that compared with the $^{99m}$Tc complex prepared from the p-substituted glucose derivative, the $^{99m}$Tc complex prepared from the m-substituted glucose derivative has lower uptake in non-target organs and higher tumor/blood ratio, tumor/muscle ratio and tumor/lung ratio, and thus is more suitable for tumor diagnosis and treatment.

In an embodiment, the benzene ring-containing glucose derivative is selected from the group consisting of:

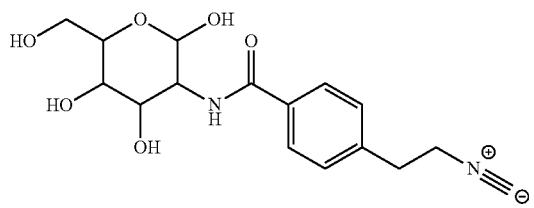

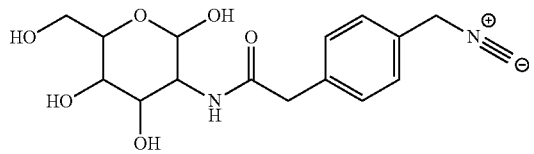

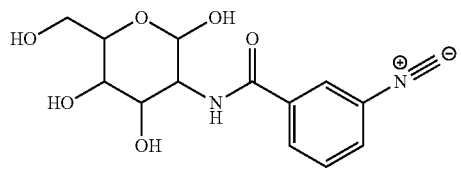

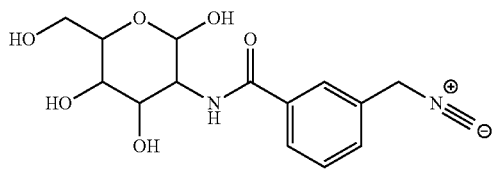

In a second aspect, this application provides a radioactive drug, comprising:
a complex formed by the benzene ring-containing glucose derivative and a radionuclide.

In an embodiment, the radionuclide is a metal radionuclide or a non-metal radionuclide.

In an embodiment, the metal radionuclide is $^{99m}$Tc, $^{99}$Tc, $^{94m}$Tc, $^{94}$Tc, $^{52}$Mn, $^{186}$Re or $^{188}$Re, and the non-metal radionuclide is $^{18}$F, $^{75}$Br, $^{76}$Br, $^{77}$Br, $^{82}$Br, $^{120}$I, $^{123}$I, $^{124}$I, $^{125}$I or $^{131}$I.

In an embodiment, the radionuclide is $^{99m}$Tc, and the complex is represented by formula (II):

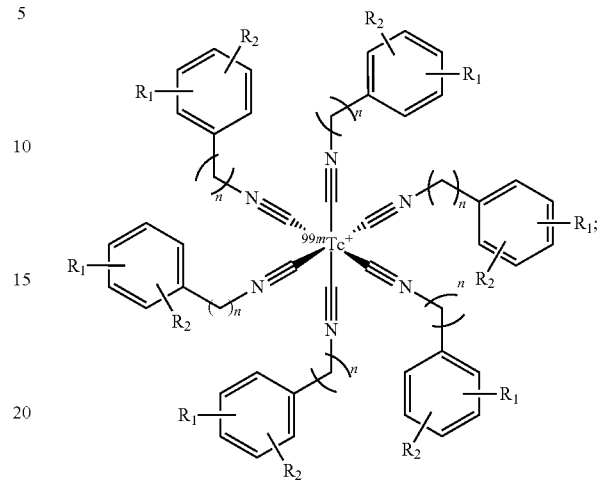

wherein $R_1$, $R_2$, $R_3$, m, n and ～ are defined as above.

In a third aspect, this application provides a tumor diagnosis method, comprising: administering the radioactive drug to a subject in need thereof; and performing imaging by single photon emission computed tomography (SPECT).

Compared with the prior art, this application has the following beneficial effects.

This application provides a benzene ring-containing glucose derivative, which is labeled with a radionuclide to obtain a radioactive drug. The radioactive drug has high uptake in tumors and excellent tumor/non-target ratio, and thus is considered as a promising tumor-imaging agent.

DETAILED DESCRIPTION OF EMBODIMENTS

A benzene ring-containing glucose derivative and a use thereof are provided herein. In an embodiment, a radioactive drug $^{99m}$Tc-CNBDG is provided, represented by:

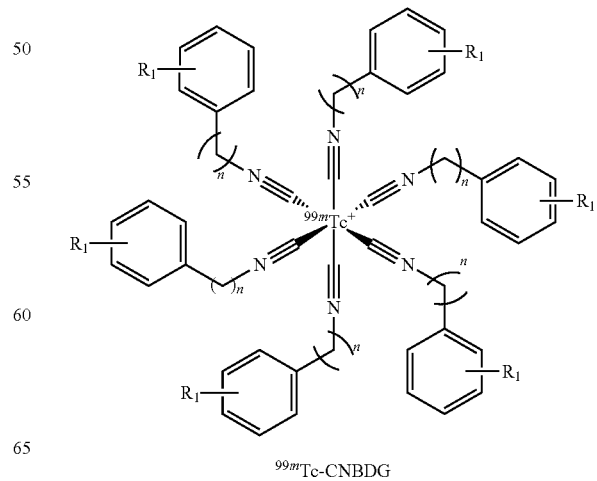

$^{99m}$Tc-CNBDG

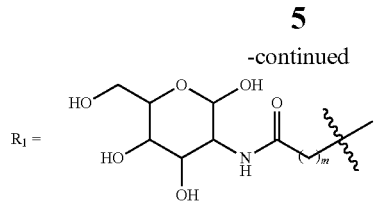

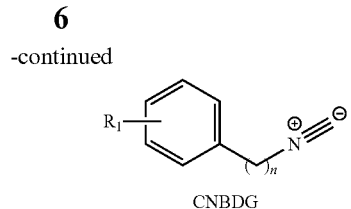

CNBDG where $R_1$ is on 3-position or 4-position of the benzene ring in the formula of $^{99m}$Tc-CNBDG;

m is 0 or 1, ∿∿∿ represents a chemical bonding between $R_1$ and the benzene ring in the formula of $^{99m}$Tc-CNBDG;

n is 0, 1 or 2; and when m=0 and n=1, $R_1$ is not on the 4-position of the benzene ring.

The preparation of the $^{99m}$Tc-CNBDG is performed as follows:

(1) Ligand Synthesis

D-glucosamine hydrochloride and NaOH were added to a 25 mL round-bottom flask, to which anhydrous methanol was added. The reaction mixture was stirred at room temperature for complete dissolution, dropwise added with a solution of Compound 1 in methanol, and reacted at room temperature for 24 h. Then the reaction mixture was concentrated by vacuum distillation, and purified by column chromatography (eluent:dichloromethane:methanol=5:1) to obtain the ligand CNBDG, as shown in the following synthesis route:

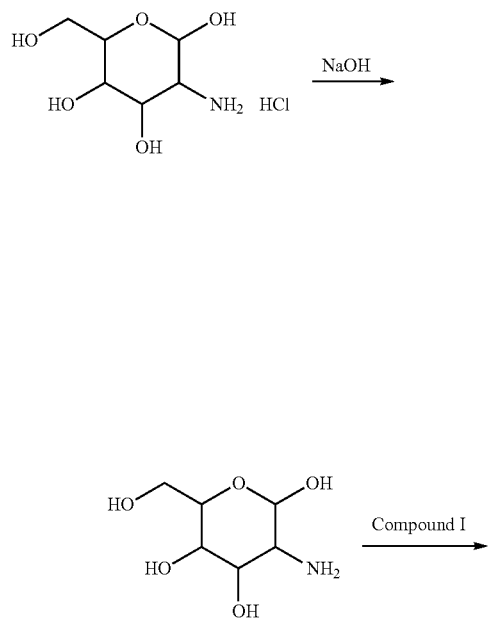

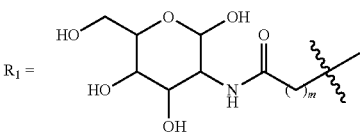

Compound 1 was shown as:

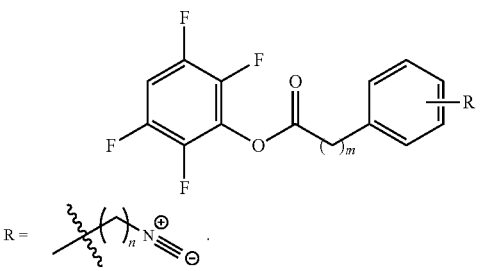

(2) Preparation of $^{99m}$Tc-CNBDG 1 mg of sodium citrate and 1 mg of L-cysteine were dissolved in a proper amount of normal saline, to which 0.06 mg of $SnCl_2 \cdot 2H_2O$ was added. The reaction mixture was adjusted to pH 6.0, added with 0.5 mg of the ligand CNBDG and 1-2 mL of freshly-eluted $Na^{99m}TcO_4$ in sequence, and then reacted at 100° C. for 20 min to obtain a $^{99m}$Tc-CNBDG complex.

The prepared $^{99m}$Tc-CNBDG complex had a radiochemical purity of greater than 90%, excellent in vivo and in vitro stability, high uptake and good retention in tumor sites of tumor-bearing mice, and a good target/non-target ratio. Compared with the $^{99m}$Tc-CNPEDG and $^{99m}$Tc-$(CN5DG)_6^+$ in the prior art, $^{99m}$Tc-CNBDG had a higher tumor/muscle ratio and a higher tumor/blood ratio, improving the target/non-target ratio of the imaging agent, and facilitating the promotion and application of $^{99m}$Tc-CNBDG as a new tumor-imaging agent.

Described below are only illustrative examples, and are not intended to limit this application. Unless otherwise specified, the operations described in the following examples shall be carried out under conventional conditions or as recommended by the manufacture.

Unless otherwise specified, the instruments used herein are all commercially-available. Unless otherwise specified, the methods used herein are conventional methods in the art, and the raw materials used herein are all commercially-available.

Example 1

Provided herein was a $^{99m}$Tc-labeled benzene ring-containing glucose derivative ($^{99m}$Tc-4-CNPeDG), represented by:

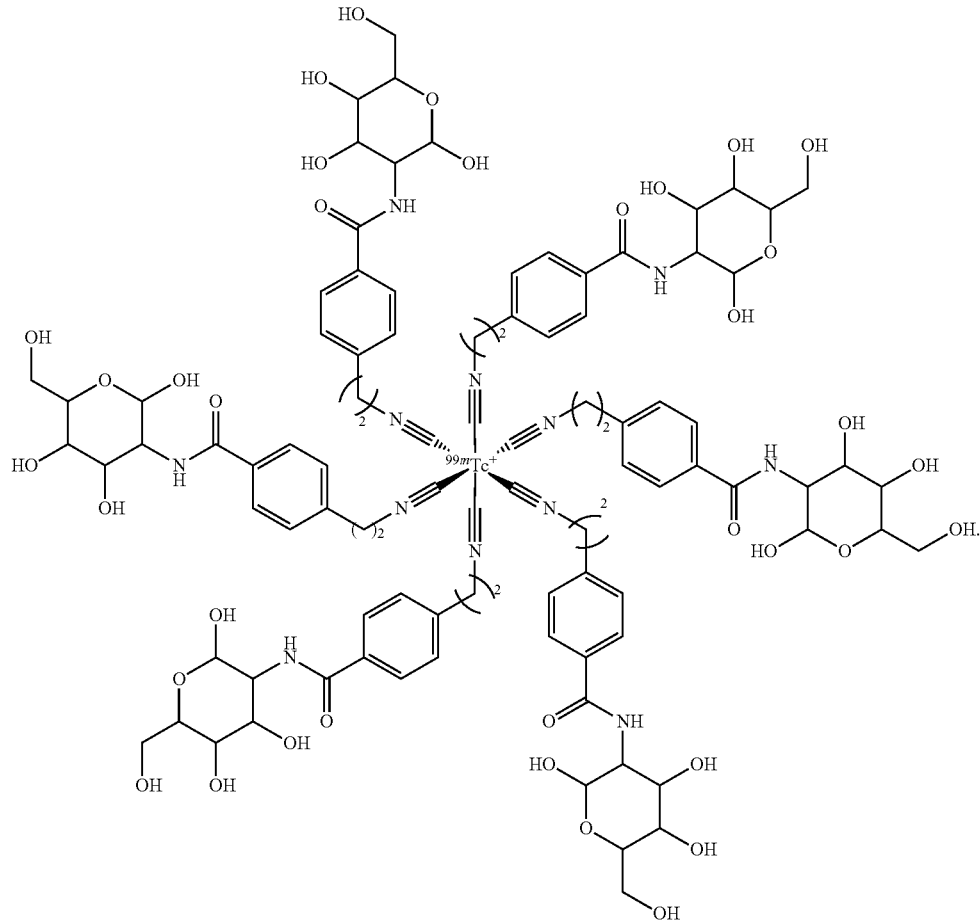

$^{99m}$Tc-4-CNPeDG was prepared as follows.

1. Synthesis of 4-CNPeDG

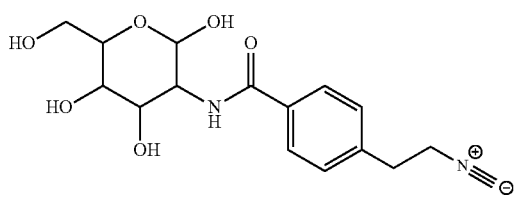 [SMILES: [C-]#[N+]CCc1ccc(C(=O)NC2C(O)OC(CO)C(O)C2O)cc1]

0.269 g of D-glucosamine hydrochloride and 0.055 g of sodium hydroxide were added to a 25 mL round-bottom flask, to which 20 mL of anhydrous methanol was added. The reaction mixture was stirred at room temperature for complete dissolution, added with 10 mL of a methanol solution containing 0.337 g of 4-(2-isocyanoethyl)-benzoic acid-2,3,5,6-tetrafluorophenylester, and reacted at room temperature for 24 h. The reaction mixture was concentrated by vacuum distillation, purified by silica gel column chromatography (eluent:dichloromethane:methanol=5:1) and dried to obtain 0.13 g of a pale yellow solid as 4-CNPeDG (37% yield).

$^1$H NMR (400 MHz, methanol-d4): δ7.83 (dd, J=15.8, 8.5 Hz, 2H), 7.37 (dd, J=22.4, 8.2 Hz, 2H), 5.25 (t, J=3.0 Hz, 1H), 4.07 (dt, J=10.7, 3.1 Hz, 1H), 3.97-3.80 (m, 3H), 3.80-3.67 (m, 2H), 3.46 (dt, J=21.3, 8.3 Hz, 2H), 3.03 (t, J=6.6 Hz, 2H).

HRMS(m/z): found 335.1252 (calc. 335.1248 for $C_{16}H_{19}N_2O_6[M-H]^-$).

IR(KBr)/cm$^{-1}$: 2146.86 (—N≡C).

2. Synthesis of $^{99m}$Tc-4-CNPeDG 1 mg of sodium citrate and 1 mg of L-cysteine were dissolved in a proper amount of normal saline, to which 0.06 mg of SnCl$_2$·2H$_2$O was added. The reaction mixture was adjusted to pH 6.0, added with 0.5 mg of 4-CNPeDG and 1-2 mL of freshly-eluted Na$^{99m}$TcO$_4$ in sequence, and then reacted at 100° C. for 20 min to obtain the $^{99m}$Tc-4-CNPeDG.

Example 2

Provided herein was a $^{99m}$Tc-labeled benzene ring-containing glucose derivative ($^{99m}$Tc-4-CNMBDG), represented by:

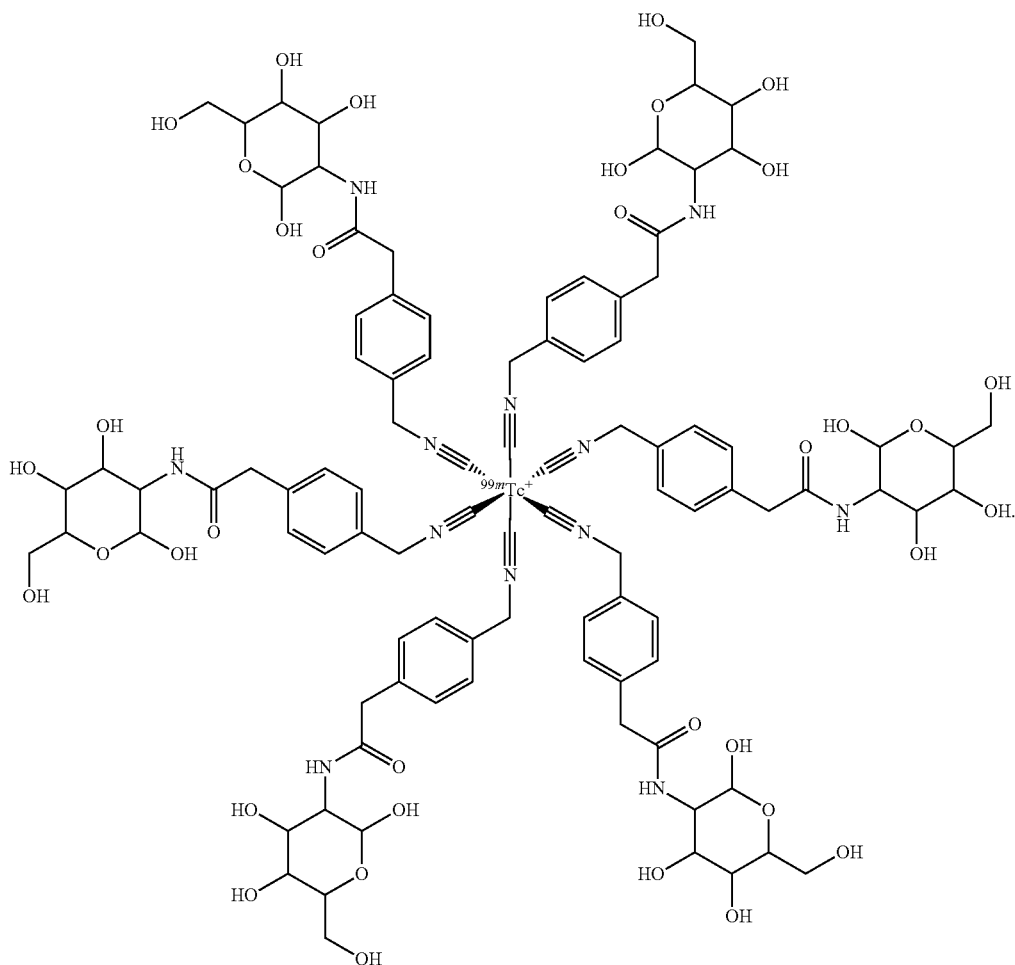

$^{99m}$Tc-4-CNMBDG was prepared as follows.

1. Synthesis of 4-CNMBDG

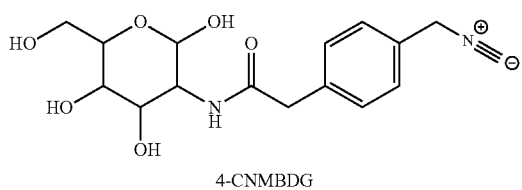 [SMILES: [C-]#[N+]Cc1ccc(CC(=O)NC2C(O)OC(CO)C(O)C2O)cc1]

4-CNMBDG 0.220 g of D-glucosamine hydrochloride and 0.045 g of sodium hydroxide were added to a 25 mL round-bottom flask, to which 10 mL of anhydrous methanol was added. The reaction mixture was stirred at room temperature for complete dissolution, added with 10 mL of a methanol solution containing 0.290 g of 2,3,5,6-tetrafluorophenyl 4-isocyanomethyl phenylacetate, and reacted at room temperature for 24 h. The reaction mixture was concentrated by vacuum distillation, purified by silica gel column chromatography (eluent:dichloromethane:methanol=5:1) and dried to obtain 0.15 g of a pale yellow solid as 4-CNMBDG (50% yield).

$^1$H-NMR (400 MHz, D$_2$O): δ7.42 (d, J=8.2 Hz, 2H), 7.37 (d, J=8.2 Hz, 2H), 5.18 (d, J=3.7 Hz, 1H), 3.98-3.82 (m, 3H), 3.81-3.74 (m, 2H), 3.74-3.63 (m, 3H), 3.60-3.37 (m, 2H).

HRMS(m/z): found 337.1398 (calc. 337.1394 for C$_{16}$H$_{21}$N$_2$O$_6$[M+H]$^+$).

IR(KBr)/cm$^{-1}$: 2152.65 (—N≡C).

2. Synthesis of $^{99m}$Tc-4-CNMBDG 1 mg of sodium citrate and 1 mg of L-cysteine were dissolved in an appropriate amount of normal saline, to which 0.06 mg of SnCl$_2$·2H$_2$O was added. The reaction mixture was adjusted to pH 6.0, added with 0.5 mg of 4-CNMBDG and 1-2 mL of freshly-eluted Na$^{99m}$TcO$_4$ in sequence, and reacted at 100° C. for 20 min to obtain the $^{99m}$Tc-4-CNMBDG.

Example 3

Provided herein was a $^{99m}$Tc-labeled benzene ring-containing glucose derivative ($^{99m}$Tc-3-CNBzDG), represented by:

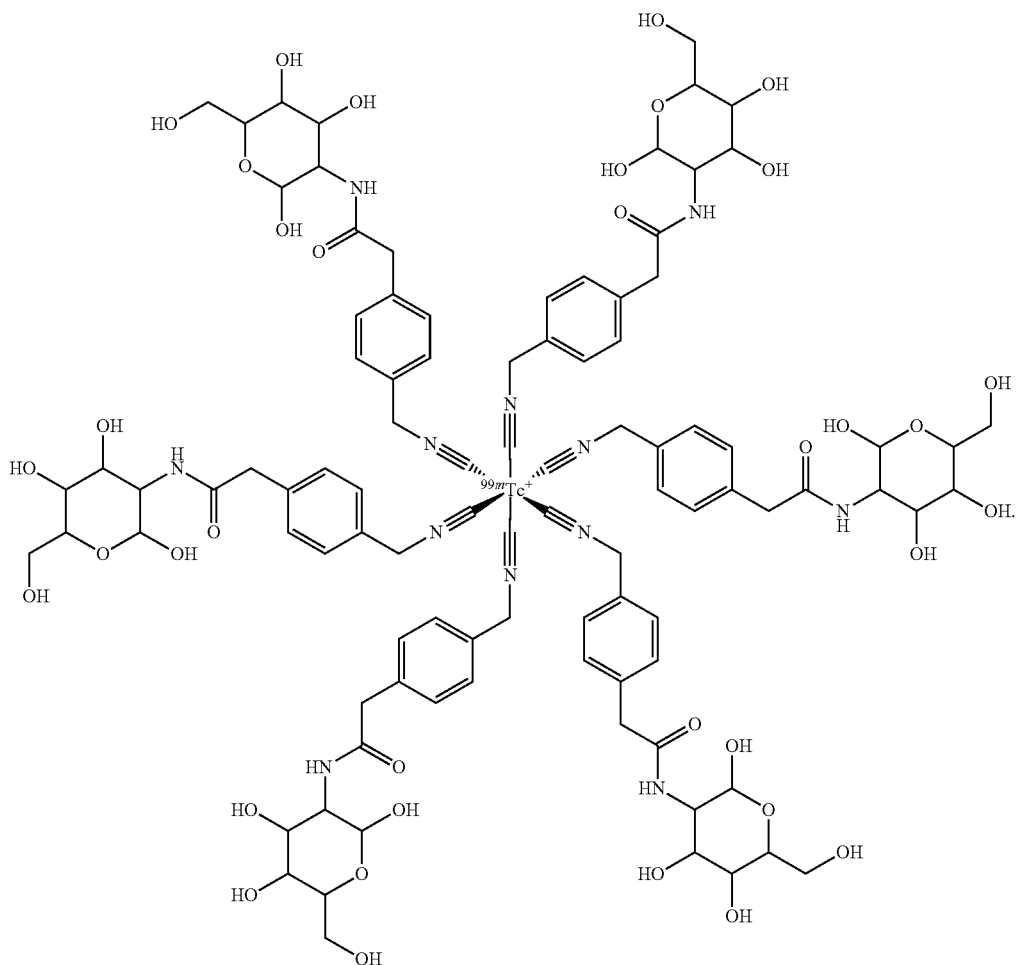

$^{99m}$Tc-3-CNBzDG was prepared as follows.

1. Synthesis of 3-CNBzDG 0.326 g of D-glucosamine hydrochloride and 0.066 g of sodium hydroxide were added to a 25 mL round-bottom flask, to which 10 mL of anhydrous methanol was added. The reaction mixture was stirred at room temperature for complete dissolution, added with 10 mL of a methanol solution containing 0.499 g of 2,3,5,6-tetrafluorophenyl 3-isocyano benzoate, and reacted at room temperature for 24 h. The reaction mixture was concentrated by vacuum distillation, purified by silica gel column chromatography (eluent:dichloromethane:methanol=5:1), and dried to obtain 0.128 g of a pale yellow solid as 3-CNBzDG (29% yield).

$^1$H-NMR (400 MHz, D$_2$O): δ7.97-7.79 (m, 2H), 7.66 (dd, J=17.2, 8.0 Hz, 1H), 7.56 (dtd, J=27.2, 7.8, 2.2 Hz, 1H), 5.34 (d, J=3.2H z, 1H), 4.13 (dd, J=10.7, 3.4 Hz, 1H), 4.03-3.89 (m, 2H), 3.89-3.74 (m, 1H), 3.62-3.44 (m, 2H).

HRMS(m/z): found 307.0939 (calc. 307.0935 for C$_{14}$H$_{15}$N$_2$O$_6$[M−H]$^−$).

IR(KBr)/cm$^{-1}$: 2127.58 (—N≡C).

2. Synthesis of $^{99m}$Tc-3-CNBzDG 1 mg of sodium citrate and 1 mg of L-cysteine were dissolved in a proper amount of normal saline, to which 0.06 mg of SnCl$_2$·2H$_2$O was added. The reaction mixture was adjusted to pH 6.0, added with 0.5 mg of 3-CNBzDG and 1-2 mL of freshly-eluted Na$^{99m}$TcO$_4$ in sequence, and then reacted at 100° C. for 20 min to obtain the $^{99m}$Tc-3-CNBzDG.

Example 4

Provided herein was a $^{99m}$Tc-labeled benzene ring-containing glucose derivative ($^{99m}$Tc-3-CNPEDG), represented by:

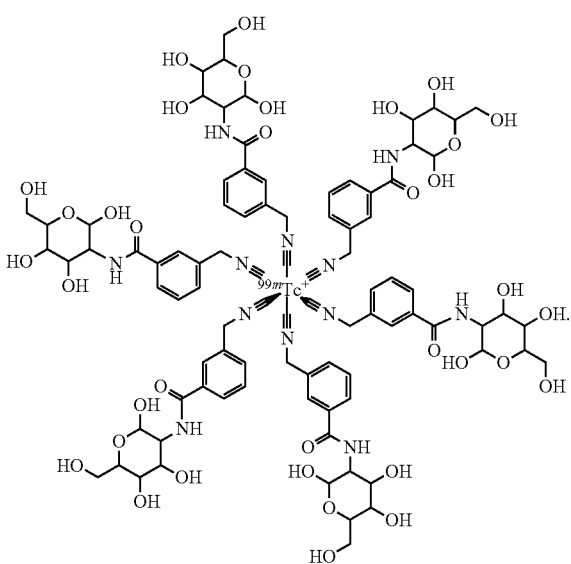

$^{99m}$Tc-3-CNPEDG was prepared as follows.

1. Synthesis of 3-CNPEDG 0.220 g of D-glucosamine hydrochloride and 0.044 g of sodium hydroxide were added to a 25 mL round-bottom flask, to which 15 mL of anhydrous methanol was added. The reaction mixture was stirred at room temperature for complete dissolution, added with 10 mL of a methanol solution containing 0.312 g of 2,3,5,6-tetrafluorophenyl 3-isocyanomethyl benzoate to obtain a reaction solution, and reacted at room temperature for 24 h. The reaction mixture was concentrated by vacuum distillation, purified by silica gel column chromatography (eluent:dichloromethane:methanol=5:1) and dried to obtain 0.119 g of pale yellow solid as 3-CNPEDG (37% yield).

$^1$H NMR (400 MHz, methanol-d4): δ7.96-7.78 (m, 2H), 7.66-7.44 (m, 2H), 5.26 (d, J=3.2 Hz, 1H), 4.84 (s, 2H), 4.08 (dd, J=10.7, 3.4 Hz, 1H), 3.99-3.79 (m, 3H), 3.74 (dd, J=11.9, 5.5 Hz, 1H), 3.41 (dt, J=30.3, 8.5 Hz, 1H).

HRMS(m/z): found 323.1241 (calc. 323.1237 for $C_{15}H_{19}N_2O_6[M+H]^+$).

IR(KBr)/cm$^{-1}$: 2156.51 (—N≡C).

2. Synthesis of $^{99m}$Tc-3-CNPEDG 1 mg of sodium citrate and 1 mg of L-cysteine were dissolved in an appropriate amount of normal saline, to which 0.06 mg of SnCl$_2$·2H$_2$O was added. The reaction mixture was adjusted to pH 6.0, added with 0.5 mg of 3-CNPEDG and 1-2 mL of freshly-eluted Na$^{99m}$TcO$_4$ in sequence, and reacted at 100° C. for 20 min to obtain the $^{99m}$Tc-3-CNPEDG.

Comparative Example 1

Provided herein was $^{99m}$Tc-CNPEDG, which was prepared according to the method provided in Chinese Patent Application Publication No. 111138504A, represented by:

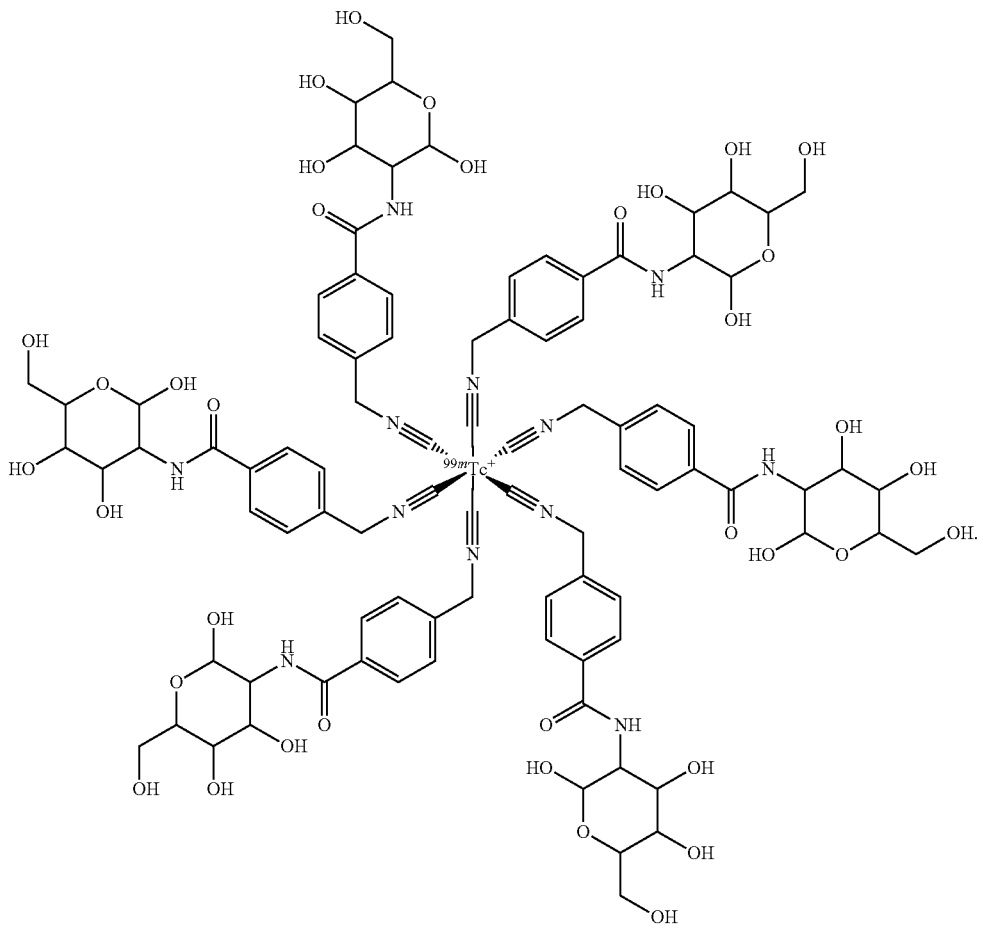

Comparative Example 2

Provided herein was $^{99m}$Tc-(CN5DG)$_6$$^+$, which was prepared according to the method provided in Chinese Patent Application Publication No. 107245087A, represented by:

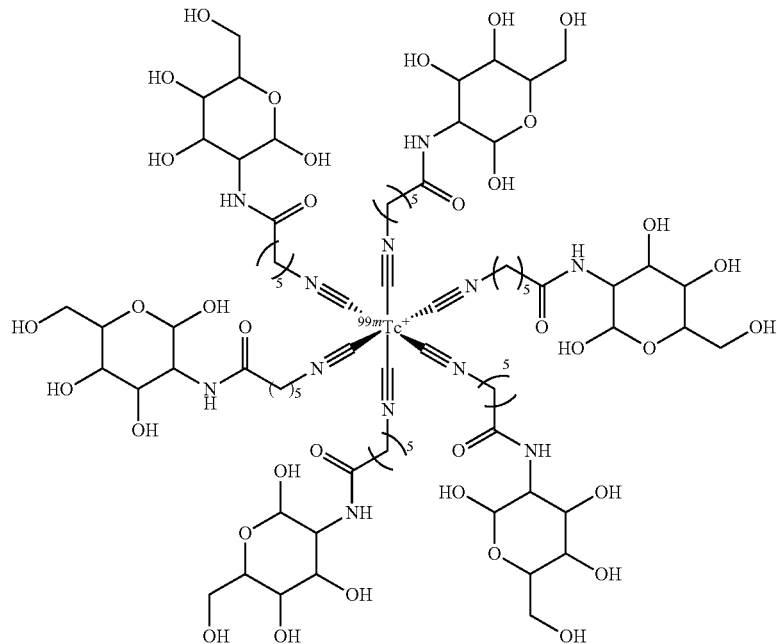

Experimental Example

1. Chromatographic identification of radioactive compounds provided in Examples 1-4

(1.1) Thin-Layer Chromatography (TLC)

Radiochemical yield and radiochemical purity of the labeled substance were tested by using TLC method, where the developing system used herein was a polyamide film-ammonium acetate (1M)/methanol system (a volume ratio of ammonium acetate to methanol was 2:1). Under such developing system, the $R_f$ (retention factor) value of each radioactive component was shown in Table 1.

TABLE 1

| $R_f$ radioactive components under a polyamide film-ammonium acetate (1M)/methanol developing system | | | |
|---|---|---|---|
| | $^{99m}$TcO$_4$$^-$ | $^{99m}$TCO$_2$ · nH$_2$0 | $^{99m}$Tc-CNBDG |
| $R_f$ value | 0-0.1 | 0-0.1 | 0.7-1.0 |

The chromatographic identification results demonstrated that the radiochemical yield and purity of the $^{99m}$Tc-CNBDG complex were both greater than 90%. The $^{99m}$Tc-CNBDG complex was used in subsequent experiments without further purification.

(1.2) High Performance Liquid Chromatography (HPLC)

The radiochemical purity of the labeled substances was identified by HPLC, where the HPLC parameters were listed as follows: SHIMADZU HPLC system (CL-20AVP); C$_{18}$ column (Kromasil, 5 μm, 250×4.6 mm); Gabi radioactivity detector (Elysia-raytest GmbH Company); elution gradient: shown in Table 2; flow rate: 1 mL/min; phase A: pure water containing 0.1% trifluoroacetic acid (TFA); and phase B: acetonitrile containing 0.1% trifluoroacetic acid.

TABLE 2

| Gradient elution program | | |
|---|---|---|
| t/min | A/% | B/% |
| 0 | 90 | 10 |
| 2 | 90 | 10 |
| 10 | 10 | 90 |
| 18 | 10 | 90 |
| 25 | 90 | 10 |

The retention time of the radioactive compounds provided in Examples 1-4 was determined by HPLC: $^{99m}$Tc-4-CNPeDG: 10.7 min; $^{99m}$Tc-4-CNMBDG: 10.6 min; $^{99m}$Tc-3-CNBzDG: 10.4 min; and $^{99m}$Tc-3-CNPEDG: 10.6 min.

2. Determination of Lipid-Water Partition Coefficient

A 2 mL centrifuge tube was added with 100 μL (10 μCi) of a labeling solution, then added with 950 μL of n-octanol and 850 μL of phosphate buffer solution (PBS, 0.025 M, pH=7.4). The 2 mL centrifuge tube was subjected to vortex for 3 min (2,500 rpm) and standing until the reaction solution was layered, and then centrifuged at 9,000 rpm for 5 min. Three samples (each for 100 μL) were collected from each of the two phases, and placed in γ-counter for the determination of radioactive counting. The lipid-water partition coefficient (P) was calculated by Organic phase radioactive counting/water phase radioactive counting, and was usually expressed as Log P. The log P values of the radioactive compounds provided in Examples 1-4 were shown in Table 3. All Log P values were negative, indicating that the samples were all water-soluble substances.

TABLE 3

Lipid-water partition coefficient of $^{99m}$Tc-CNBDG complexes

|  | $^{99m}$Tc-4-CNPeDG | $^{99m}$Tc-4-CNMBDG | $^{99m}$Tc-3-CNBzDG | $^{99m}$Tc-3-CNPEDG |
|---|---|---|---|---|
| Log P | −3.593 ± 0.012 | −3.097 ± 0.036 | −3.743 ± 0.038 | −3.389 ± 0.166 |

3. Stability Determination (3.1) In Vitro Stability

The radioactive complexes provided in Examples 1-4 were respectively placed in normal saline (room temperature) and mouse serum (37° C.) for 4 h, and then analyzed by HPLC for the radiochemical purity. The results indicated that whether kept in normal saline (room temperature) or mouse serum (37° C.) for 4 h, the radioactive samples provided in Examples 1-4 all had a radiochemical purity above 90%, suggesting good in vitro stability.

(2) In Vivo Stability

Solutions (0.1-0.2 mL, 74 MBq) containing the radioactive samples of Examples 1-4 were respectively injected into the mice via the tail vein. One hour later, the mice were sacrificed by decapitation, and the urine and blood were harvested, and measured for radiochemical purity by HPLC. The results showed that the radiochemical purity of $^{99m}$Tc-CNBDG complex in urine and blood was still greater than 90% at 1 h post administration, suggesting good in vivo stability.

4. Biodistribution in Tumor-Bearing Mice

The mice bearing S180 tumors were injected intravenously via the tail vein respectively with the solutions (0.1 mL, 370 kBq) containing the radioactive drugs of Examples 1-4. The mice bearing S180 tumors were sacrificed by decapitation at different time points (30 min, 120 min) after the injection (5 mice for each time point). After dissection, the heart, liver, lung, kidney, spleen, bone, muscle, small intestine, blood and tumors were harvested, and measured for radioactivity with the γ-counter. The biodistribution individual organs or tissues was expressed as the percentage of the injected dose per gram of organ or tissue (% ID/g). The biodistribution results of the labeled substances in tumor-bearing mice were shown in Tables 4-7.

TABLE 4

Biodistribution of $^{99m}$Tc-4-CNPeDG in mice bearing S180 tumor (n = 5, mean ± SD, % ID/g)

|  | 30 min | 120 min |
|---|---|---|
| Heart | 1.15 ± 0.04 | 0.15 ± 0.02 |
| Liver | 0.95 ± 0.03 | 0.38 ± 0.08 |
| Lung | 2.80 ± 0.13 | 0.23 ± 0.03 |
| Kidney | 7.32 ± 0.90 | 2.98 ± 0.74 |
| Spleen | 0.70 ± 0.02 | 0.17 ± 0.03 |
| Bone | 1.10 ± 0.07 | 0.18 ± 0.03 |
| Muscle | 0.68 ± 0.05 | 0.10 ± 0.02 |
| Small intestine | 1.38 ± 0.20 | 0.31 ± 0.07 |
| Tumor | 2.80 ± 0.04 | 0.95 ± 0.21 |
| Blood | 2.42 ± 0.16 | 0.10 ± 0.04 |
| Thyroid (% ID/g) | 0.02 ± 0.00 | 0.003 ± 0.001 |
| Tumor/muscle ratio | 4.16 ± 0.35 | 9.69 ± 1.81 |
| Tumor/blood ratio | 1.16 ± 0.09 | 10.17 ± 1.95 |

TABLE 5

Biodistribution of $^{99m}$Tc-4-CNMBDG in mice bearing S180 tumor (n = 5, mean ± SD, % ID/g)

|  | 30 min | 120 min |
|---|---|---|
| Heart | 2.67 ± 0.41 | 1.31 ± 0.18 |
| Liver | 3.00 ± 0.55 | 2.43 ± 0.49 |
| Lung | 5.89 ± 0.59 | 1.31 ± 0.44 |
| Kidney | 10.18 ± 1.28 | 7.37 ± 1.71 |
| Spleen | 2.24 ± 0.38 | 1.28 ± 0.34 |
| Bone | 3.05 ± 0.62 | 1.27 ± 0.35 |
| Muscle | 1.96 ± 0.50 | 0.86 ± 0.15 |
| Small intestine | 4.04 ± 0.87 | 1.65 ± 0.43 |
| Tumor | 6.46 ± 1.86 | 6.22 ± 1.77 |
| Blood | 4.08 ± 0.57 | 0.64 ± 0.22 |
| Thyroid (% ID/g) | 0.07 ± 0.01 | 0.03 ± 0.01 |
| Tumor/muscle ratio | 3.52 ± 1.35 | 7.14 ± 1.11 |
| Tumor/blood ratio | 1.57 ± 0.36 | 10.06 + 1.54 |

TABLE 6

Biodistribution of $^{99m}$Tc-3-CNBzDG in mice bearing S180 tumor (n = 5, mean ± SD, % ID/g)

|  | 30 min | 120 min |
|---|---|---|
| Heart | 1.44 ± 0.21 | 0.54 ± 0.07 |
| Liver | 1.38 ± 0.24 | 0.89 ± 0.09 |
| Lung | 4.00 ± 0.52 | 0.76 ± 0.20 |
| Kidney | 6.69 ± 0.68 | 4.49 ± 0.56 |
| Spleen | 1.06 ± 0.27 | 0.43 ± 0.17 |
| Bone | 1.44 ± 0.29 | 0.42 ± 0.03 |
| Muscle | 0.77 ± 0.06 | 0.24 ± 0.05 |
| Small intestine | 2.05 ± 0.29 | 0.70 ± 0.10 |
| Tumor | 2.51 ± 0.52 | 1.47 ± 0.22 |
| Blood | 2.53 ± 0.83 | 0.27 ± 0.02 |
| Thyroid (% ID/g) | 0.03 ± 0.01 | 0.01 ± 0.00 |
| Tumor/muscle ratio | 3.28 ± 0.66 | 6.16 ± 0.71 |
| Tumor/blood ratio | 1.04 ± 0.22 | 5.39 ± 0.79 |

TABLE 7

In vivo biodistribution of $^{99m}$Tc-3-CNPEDG in mice bearing S180 tumor (n = 5, mean ± SD, % ID/g)

|  | 30 min | 120 min |
|---|---|---|
| Heart | 1.18 ± 0.12 | 0.23 ± 0.05 |
| Liver | 1.30 ± 0.06 | 0.68 ± 0.07 |
| Lung | 3.10 ± 0.22 | 0.42 ± 0.09 |
| Kidney | 9.69 ± 3.48 | 4.70 ± 0.81 |
| Spleen | 0.86 ± 0.09 | 0.25 ± 0.06 |
| Bone | 1.26 ± 0.23 | 0.30 ± 0.06 |
| Muscle | 0.82 ± 0.24 | 0.16 ± 0.04 |
| Small intestine | 2.19 ± 0.69 | 0.43 ± 0.11 |
| Tumor | 2.72 ± 0.36 | 1.35 ± 0.20 |
| Blood | 2.82 ± 0.30 | 0.22 ± 0.07 |
| Thyroid (% ID/g) | 0.04 ± 0.01 | 0.01 ± 0.00 |
| Tumor/muscle ratio | 3.49 ± 0.71 | 8.76 ± 1.14 |
| Tumor/blood ratio | 0.97 ± 0.07 | 6.40 ± 1.45 |

Referring to Tables 4-7, the results showed that the radioactive drugs provided in Examples 1-4 had good retention in tumors, and were rapidly metabolized in non-target organs. The tumor/muscle and tumor/blood ratios were higher at 120 min postinjection.

The radioactive drugs provided in Examples 1-4 were compared with the $^{99m}$Tc-CNPEDG in Comparative Example 1 and $^{99m}$Tc-(CN5DG)$_6^+$ provided in Comparative Example 2 in terms of the biodistribution in tumor-bearing mice, and the results were shown in Table 8.

TABLE 8

Comparison of Examples 1-4, and Comparative Examples 1-2 in terms of biodistribution in mice bearing S180 tumor (120 min p.i., % ID/g, mean ± SD)

| | $^{99m}$Tc-4-CNPeDG | $^{99m}$Tc-4-CNMBDG | $^{99m}$Tc-3-CNBzDG |
|---|---|---|---|
| Liver | 0.38 ± 0.08 | 2.43 ± 0.49 | 0.89 ± 0.09 |
| Lung | 0.23 ± 0.03 | 1.31 ± 0.44 | 0.76 ± 0.20 |
| Kidney | 2.98 ± 0.74 | 7.37 ± 1.71 | 4.49 ± 0.56 |
| Muscle | 0.10 ± 0.02 | 0.86 ± 0.15 | 0.24 ± 0.05 |
| Tumor | 0.95 ± 0.21 | 6.22 ± 1.77 | 1.47 ± 0.22 |
| Blood | 0.10 ± 0.04 | 0.64 ± 0.22 | 0.27 ± 0.02 |
| Tumor/muscle ratio | 9.69 ± 1.81 | 7.14 ± 1.11 | 6.16 ± 0.71 |
| Tumor/blood ratio | 10.17 ± 1.95 | 10.06 ± 1.54 | 5.39 ± 0.79 |
| Liver | 0.68 ± 0.07 | 2.52 ± 0.26 | 0.34 ± 0.08 |
| Lung | 0.42 ± 0.09 | 2.39 ± 0.31 | 0.29 ± 0.06 |
| Kidney | 4.70 ± 0.81 | 7.56 ± 0.94 | 2.07 ± 0.13 |
| Muscle | 0.16 ± 0.04 | 0.82 ± 0.08 | 0.18 ± 0.03 |
| Tumor | 1.35 ± 0.20 | 4.25 ± 0.56 | 0.75 ± 0.07 |
| Blood | 0.22 ± 0.07 | 1.29 ± 0.16 | 0.16 ± 0.02 |
| Tumor/muscle ratio | 8.76 ± 1.14 | 5.21 ± 0.50 | 4.16 |
| Tumor/blood ratio | 6.40 ± 1.45 | 3.29 ± 0.12 | 4.69 |

Referring to the results shown in Table 7, the tumor uptake and target/non-target ratio of the radioactive drugs provided in Examples 1-4 were higher than those of $^{99m}$Tc-(CN5DG)$_6^+$. Although $^{99m}$Tc-4-CNPeDG, $^{99m}$Tc-3-CNBzDG, $^{99m}$Tc-3-CNPEDG had lower tumor uptake than $^{99m}$Tc-CNPEDG, but they had lower uptake and larger metabolic rate in non-target organs, leading to a better target/non-target ratio. It was worth noting that $^{99m}$Tc-4-CNMBDG had higher tumor uptake and faster clearance in blood, thereby greatly improving the tumor/blood ratio.

Additionally, it was found that compared with the p-substituted $^{99m}$Tc complexes (such as $^{99m}$Tc-4-CNBzDG and $^{99m}$Tc-4-CNPEDG), the m-substituted $^{99m}$Tc complexes (such as $^{99m}$Tc-3-CNBzDG and $^{99m}$Tc-3-CNPEDG) had higher tumor/muscle ratio, tumor/blood ratio and tumor/lung ratio (see Table 9).

TABLE 9

Comparison of target/non-target ratios of $^{99m}$Tc-3-CNPEDG, $^{99m}$Tc-4-CNPEDG, $^{99m}$Tc-3-CNBzDG and $^{99m}$Tc-4-CNBzDG (120 min p.i., mean ± SD)

| R$_1$ | $^{99m}$Tc-3-CNPEDG Meta-position | $^{99m}$Tc-4-CNPEDG Para-position | $^{99m}$Tc-3-CNBzDG Meta-position | $^{99m}$Tc-4-CNBzDG Para-position |
|---|---|---|---|---|
| Tumor/muscle ratio | 8.76 ± 1.14 | 5.21 ± 0.50 | 6.16 ± 0.71 | 2.34 ± 0.18 |
| Tumor/blood ratio | 6.40 ± 1.45 | 3.29 ± 0.12 | 5.39 ± 0.79 | 0.47 ± 0.02 |
| Tumor/lung ratio | 3.26 ± 0.37 | 1.81 ± 0.30 | 2.01 ± 0.35 | 0.49 ± 0.02 |

Note: the difference between $^{99m}$Tc-4-CNPEDG and $^{99m}$Tc-3-CNPEDG was only in the R$_1$ substitution site, and so was the difference between $^{99m}$Tc-4-CNBzDG and $^{99m}$Tc-3-CNBzDG.

Described above are merely preferred embodiments of the application, which are not intended to limit the application. Although the disclosure has been described in detail above, those skilled in the art can still make various variations, modifications and replacements to the embodiments provided herein. It should be understood that any modifications or improvements made by those skilled in the art without departing from the spirit of the application shall fall within the scope of the present application defined by the appended claims.

What is claimed is:

1. A benzene ring-containing glucose derivative of formula (I):

wherein one or two R$_1$ are located on a benzene ring in formula (I);

the one or two R$_1$ are each independently when there is one R$_1$, R$_1$ is on 3-position or 4-position of the benzene ring in formula (I); when there are two R$_1$, the two R$_1$ are on 3-position and 4-position of the benzene ring, respectively;

R$_3$ is hydrogen;

m is 0 or 1; and ∿∿∿ represents chemical bonding between R$_1$ and the benzene ring in formula (I);

R$_2$ is hydrogen;

n is 0, 1 or 2; and when m=0 and n=1, R$_1$ is not on the 4-position of the benzene ring.

2. The benzene ring-containing glucose derivative of claim 1, wherein the sum of m and n is 2.

3. The benzene ring-containing glucose derivative of claim 1, wherein there is one R$_1$, and the one R$_1$ is on the 3-position of the benzene ring.

4. A radioactive drug, comprising:

a complex formed by a benzene ring-containing glucose derivative and a radionuclide;

wherein:

the radionuclide is $^{99m}$Tc;

the benzene ring-containing glucose derivative is represented by formula (I):

; and and
the complex is represented by formula (II):

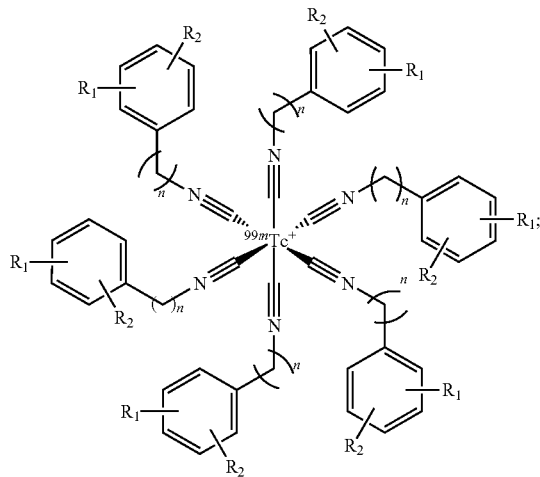
(II)

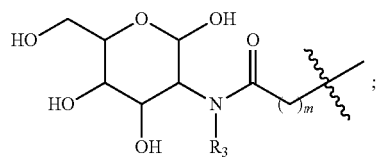

wherein in formula (I) and formula (II):
one or two $R_1$ are located on each of benzene rings;
the one or two $R_1$ are each independently wherein when there is one $R_1$, $R_1$ is on 3-position or 4-position of each of the benzene rings; when there are two $R_1$, the two $R_1$ are on 3-position and 4-position of each of the benzene rings, respectively;

$R_3$ is hydrogen;

m is 0 or 1; and ⁓⁓⁓ represents chemical bonding between $R_1$ and each of the benzene rings;

$R_2$ is hydrogen;

n is 0, 1 or 2; and when m=0 and n=1, $R_1$ is not on the 4-position of each of the benzene rings.

5. A tumor imaging method, comprising:
administering the radioactive drug of claim 4 to a subject in need thereof; and
performing imaging of the subject by single photon emission computed tomography (SPECT).

* * * * *